United States Patent [19]

Hubele et al.

[11] 4,101,672
[45] Jul. 18, 1978

[54] MICROBICIDAL ALANINE THIOESTERS

[75] Inventors: Adolf Hubele, Magden; Walter Kunz, Oberwil, both of Switzerland; Wolfgang Eckhardt, Lörrach, Fed. Rep. of Germany

[73] Assignee: Ciba-Geigy Corporation, Ardsley, N.Y.

[21] Appl. No.: 725,203

[22] Filed: Sep. 22, 1976

[30] Foreign Application Priority Data

Sep. 30, 1975 [CH] Switzerland ............... 12647/75

[51] Int. Cl.² ............... A01N 9/12; C07C 153/11; C07C 161/02
[52] U.S. Cl. ............... 424/301; 260/455 R; 260/454
[58] Field of Search ............... 260/455 R; 424/301

[56] References Cited

U.S. PATENT DOCUMENTS

| | | | |
|---|---|---|---|
| 3,048,626 | 8/1962 | Wallingford | 260/471 R |
| 3,413,340 | 11/1968 | Wallingford | 260/519 |
| 3,712,805 | 1/1973 | Yates et al. | 71/98 |
| 3,766,244 | 10/1973 | Giacobbe et al. | 424/301 |
| 3,832,383 | 8/1974 | Olin | 260/455 R |

Primary Examiner—Lewis Gotts
Assistant Examiner—Molly C. Eakin
Attorney, Agent, or Firm—Frederick H. Rabin

[57] ABSTRACT

New glycine and alanine thioesters of the formula

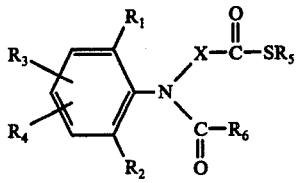

wherein $R_1$ and $R_2$ each represent $C_1$-$C_4$-alkoxy or halogen,
$R_3$ represents hydrogen, $C_1$-$C_3$-alkyl or halogen,
$R_4$ represents hydrogen or methyl,
$R_5$ represents methyl or ethyl,
$R_6$ represents hydrogen, $C_1$-$C_6$-alkyl which is unsubstituted or substituted by cyano or thiocyano, $C_2$-$C_4$-alkyl which is substituted by halogen, $C_2$-$C_5$-alkenyl which is unsubstituted or substituted by halogen, $C_2$-$C_4$-alkynyl or $C_3$-$C_7$-cycloalkyl, and
X represents

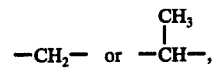

with the proviso that the total number of carbon atoms contained by the groups $R_1$, $R_2$, $R_3$ and $R_4$ does not exceed 8, a $C_2$-$C_4$-alkyl which is substituted by halogen, are effective microbicides. They may be used for controlling phytopathogenic fungi or for preventing plants from attack by fungi.

20 Claims, No Drawings

MICROBICIDAL ALANINE THIOESTERS

The present invention provides compounds of the formula I

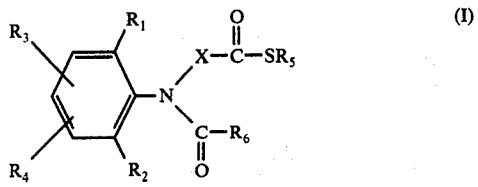

wherein
- $R_1$ and $R_2$ represent a $C_1-C_4$-alkyl group, a $C_1-C_4$-alkoxy group or a halogen atom,
- $R_3$ represents a hydrogen atom, a $C_1-C_3$-alkyl group or a halogen atom,
- $R_4$ represents a hydrogen atom or a methyl group,
- $R_5$ represents a methyl or ethyl group,
- $R_6$ represents a hydrogen atom, a $C_1-C_6$-alkyl group which is unsubstituted or substituted by cyano or thiocyano, a $C_2-C_4$-alkyl which is substituted by halogen, $C_2-C_5$-alkenyl group which is unsubstituted or substituted by halogen, a $C_2-C_4$-alkynyl or $C_3-C_7$-cycloalkyl group, and
- X represents $-CH_2-$ or

with the proviso that the total number of carbon atoms contained by the groups $R_1$, $R_2$, $R_3$ and $R_4$ does not exceed 8, a process for the manufacture thereof, microbicidal compositions which contain these compounds as active component, and a method of controlling fungi and bacteria, which comprises the use of said compounds.

By alkyl or alkyl moiety of an alkoxy group are meant the following groups, depending on the stated number of carbon atoms: methyl, ethyl, propyl, butyl, pentyl or hexyl and isomers thereof, for example isopropyl, isobutyl, sec. butyl or tert. butyl, 1-methyl-butyl etc. Where these groups are represented by $R_6$, they can, as stated, be unsubstituted or substituted by cyano or thiocyano (-SCN) or by halogen.

By alkenyl and alkynyl are meant for example the following groups: vinyl, propenyl, allyl, propargyl, butenyl, 4-pentenyl.

As a cycloalkyl group, the cyclopropyl group is particularly preferred. The term "halogen atom" is to be understood as meaning a fluorine, chlorine, bromine and iodine atom.

Particularly preferred microbicidal compounds of the formula I are those wherein X represents

These compounds shall be referred to as group Ia. An interesting group of compounds on account of their action comprises those compounds of the subgroup Ia, wherein $R_1$ represents a methyl or methoxy group, $R_2$ represents a methyl group, an ethyl group, a chlorine or bromine atom, $R_3$ represents a hydrogen atom, a methyl group or a halogen atom, $R_4$ represents a hydrogen atom or a methyl group, and $R_5$ represents a methyl or ethyl group, whilst $R_6$ represents a hydrogen atom, a $C_2-C_3$-alkyl group, a $C_1-C_3$-alkyl group which is substituted by cyano or thiocyano, a $C_2-C_3$-alkyl group which is substituted by halogen, a $C_2-C_4$alkenyl group which is unsubstituted or substituted by halogen, or also a $C_2-C_4$-alkynyl group or a cycloalkyl group. These compounds shall be referred to as group Ib.

Included within the scope of the compounds of Group Ib are those in which $R_3$ represents a hydrogen atom, a methyl group or a fluorine, chlorine or bromine atom, and $R_5$ represents a methyl group, whilst $R_6$ represents an n-propyl, β-chloroethyl or β-cyanoethyl group.

Another interesting subgroup of compounds on account of their microbicidal action comprises those compounds of the group Ia, wherein
- $R_1$ represents a methyl group,
- $R_2$ represents a methyl or ethyl group or a chlorine atom,
- $R_3$ represents a hydrogen atom, a $C_1-C_3$-alkyl group or a halogen atom,
- $R_4$ represents a hydrogen atom or a methyl group,
- $R_5$ represents a methyl group, and
- $R_6$ represents a $C_2-C_4$-alkyl, $C_2-C_4$-alkenyl or cycloalkyl group, with the proviso that the total number of carbon atoms contained by the substituents $R_1$, $R_2$, $R_3$ and $R_4$ in the phenyl ring does not exceed 4. These compounds shall be referred to as group Ic.

The compounds are obtained for example by initially reacting an aniline of the formula II

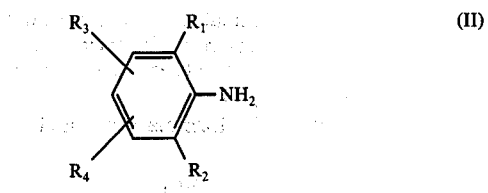

with a compound of the formula III $$Hal-X-COSR_5 \qquad (III)$$

and, in accordance with the invention, reacting the resultant compound of the formula IV

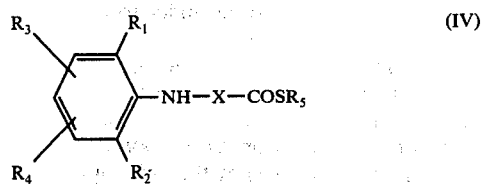

with a compound of the formula V $$HO-COR_6 \qquad (V)$$

or with the reactive acid halide, acid anhydride, ester or amide thereof, preferably with the halide or anhydride.

In the above formulae, the symbols $R_1$, $R_2$, $R_3$, $R_4$, $R_5$, $R_6$ and X are as defined in formula I, whilst "Hal" in formula III represents a halogen atom, preferably a chlorine or bromine atom. Preferred acid halides derived from compounds of the formula V are the acid chlorides or acid bromides.

The reactions can be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ethers and ethereal compounds, such as dialkyl ethers, dioxane, tetrahydrofurane; nitriles, such as acetonitrile; N,N-dialkylated amides, such as dimethyl formamide; dimethyl sulphoxide; ketones, such as methyl ethyl ketone, and mixtures of such solvents.

The reaction temperatures are between 0° and 180° C, preferably between 20° C and 120° C. It is often advantageous to use acid acceptors or condensation agents. Suitable examples are: tertiary amines, such as trialkylamines (for example triethylamine), pyridine and pyridine bases, or inorganic bases, such as the oxides and hydroxides, hydrogen carbonates and carbonates of alkali metals and alkaline earth metals, and sodium acetate. Moreover, it is also possible to use an excess of the respective aniline derivative of the formula II as acid acceptor.

The reaction step of the present invention comprising the acylation of the compounds of the formula II can also be carried out without acid acceptors. When using the acid halide of the formula V, it is advantageous to introduce nitrogen in order to expel the hydrogen halide that has formed. If the reaction is carried out without an acid acceptor, dimethyl formamide is normally used as catalyst.

Particulars on the manufacture of the intermediates of the formula IV can be inferred from those methods which are generally indicated for the manufacture of anilinoalkanoic acid esters in the following publications:

J. Org. Chem. 30, 4101 (1965); Tetrahedron 1967, 487; Tetrahedron 1967, 493.

The compounds of the formula I in which

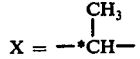

$$X = -\overset{CH_3}{\underset{|}{*CH}}-$$

contain an asymmetrical carbon atom (*). If optically active starting materials are not used to obtain these compounds, then a diastereomeric mixture is always obtained. Unless stated to the contrary in this specification, mention of one of the active substances of the formula I is always to be understood as meaning the diastereomeric mixture.

The pure optical form of the compounds of the formula I is obtained by preparing for example from the aniline of the formula II and the α-halogenopropionic acid, for example α-bromopropionic acid, the corresponding racemic form of the anilinopropionic acid of the formula VI

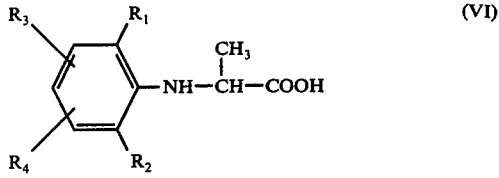

(VI)

and reacting it in known manner with a nitrogen-containing optically active base. One of the enantiomeric forms of the corresponding compound of the formula I is obtained by fractional crystallisation of the resultant salt and subsequent liberation of the optical D-antipode, optionally also by repeating the reaction with the optically active base. From this enantiomeric form it is then possible to obtain in known manner the optically active ester of the formula IV, for example in the presence of HCl or H₂SO₄, with methyl mercaptan or ethyl mercaptan, or preferably with the salts thereof, especially the sodium or potassium salts and with the acid halide of the optical antipode of the formula VI. This ester is then reacted in accordance with the invention with the corresponding compound of the formula V. The different diastereoisomers of the formula I can thus be systematically prepared. A suitable optically active organic base is α-phenylethylamine.

Instead of fractional crystallisation, the enantiomeric D-forms of the formula IV can also be obtained by diazotising the amino group in the naturally occurring L-aniline in the presence, for example, of HCl or HBr and thereby replacing it by halogen accompanied by the splitting off of N₂ and with retention of the L-configuration, thereafter effecting esterification with methyl mercaptan or ethyl mercaptan and then reacting the ester with the aniline of the formula II, when almost total inversion to the D-configurations of the formula IV occurs (cf. J.Am.Chem. Soc. 76, 6056).

The compounds of the formula I are suitable, inter alia, for controlling a variety of plant and animal pests. Their action on microorganisms, such as phytopathogenic fungi, must be singled out for special mention. Thus the compounds of the formula I have both a preventive and curative action on phytopathogenic fungi on cultivated plants, for example cereals, maize, rice, vegetables, sugar-beet, soya, ground nuts, fruit trees, ornamentals, but principally vines, hops, cucumber plants (cucumber, marrows, melons) and solanacease, such as potatoes, tobacco and tomatoes, as well as banana, cocoa and natural rubber plants.

With the active substances of the formula I it is possible to destroy the fungi which occur in plants or parts of plants (fruit, blossoms, leaves, stems, tubers, roots) and also to protect from such fungi the parts of plants which grow later. The active substances are effective against the phytopathogenic fungi which belong to the following classes: Ascomycetes; Basidiomycetes, above all rust fungi; fungi imperfecti; but especially against the Oomycetes which belong to the class of the Phycomycetes, for example Phytophthora, Peronospora, Pseudoperonospora, Pythium or Plasmopara. In addition, the compounds of the formula I have a systemic action. They can also be used as seed-dressing agents for protecting seeds (fruit, tubers, kernels) and plant cuttings from fungus infections.

Where X represents

$$-\overset{CH_3}{\underset{|}{CH}}-,$$

the enantiomeric D-forms of the formula I generally have a more pronounced microbicidal action.

It will be readily understood that the compounds of the formula I can be used together with other suitable pesticides, for example fungicides, insecticides, acaricides or active substances which influence plant growth, in order to adapt them to prevailing circumstances and to broaden their activity spectrum. The compounds of the formula I can be used by themselves or together with suitable carriers and/or other additives. Suitable carriers and additives can be solid or liquid and correspond to the customary substances used in the art of formulation, for example natural or regenerated mineral substances, solvents, dispersants, wetting agents, tackifiers, thickeners, binders or fertilisers.

The compositions according to the invention are obtained in known manner by intimately mixing and grinding the constituents.

For application, the active substances may take, and be used in, the following forms:

Solid forms:
dusts, tracking agents, granules, coated granules, impregnated granules and homogeneous granules.

Liquid forms:
a. active substance concentrates which are dispersible in water: wettable powders, pastes, emulsions, concentrated solutions;
b. solutions: aerosols.

The content of active substance in the above described compositions is between 0.1% and 95%. The active substances of the formula I can be formulated, for example, as follows:

Dusts: The following substances are used to prepare (a) 50% and (b) a 2% dust:
5 parts of active substance 95 parts of talc;
2 parts of active substance 1 part of highly dispersed silicic acid 97 parts of talc. The active substances are mixed with the carriers and ground and in this form can be processed to dusts for application.

Granulate: The following substances are used to prepare a 5% granulate:
5 parts of active substance
0.25 part of epichlorohydrin
0.25 part of cetyl polyglycol ether
3.50 parts of polyethylene glycol
91 parts of kaolin (particle size 0.3 - 0.8 mm).
The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such microgranules are advantageously used for combating soil fungi.

Wettable powders: The following constituents are used to prepare (a) a 70%, (b) a 40%, (c) and (d) a 25% and (e) a 10% wettable powder:
a. 70 parts of active substance 5 parts of sodium dibutyl naphthylsulphonate 3 parts of naphthalenesulphonic acid/phenolsulphonic acid/formaldehyde condensate (3:2:1) 10 parts of kaolin 12 parts of Champagne chalk
b. 40 parts of active substance 5 parts of sodium lignin sulphonate 1 part of sodium dibutylnaphthalenesulphonic acid 54 parts of silicic acid
c. 25 parts of active substance 4.5 parts of calcium lignin sulphonate 1.9 parts of a Champagne chalk-/hydroxyethyl cellulose mixture (1:1) 1.5 parts of sodium dibutylnaphthalenesulphonate 19.5 parts of silicic acid 19.5 parts of Champagne chalk 28.1 parts of kaolin
d. 25 parts of active substance 2.5 parts of isooctylphenoxy-polyethylene-ethanol 1.7 parts of a Champagne chalk/hydroxyethyl cellulose mixture (1:1) 8.3 parts of sodium aluminum silicate 16.3 parts of kieselguhr 46 parts of kaolin
e. 10 parts of active substance 3 parts of a mixture of the sodium salts of saturated fatty alcohol sulphates 5 parts of naphthalenesulphonic acid/formaldehyde condensate 82 parts of kaolin. The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

Emulsifiable concentrates: The following substances are used to prepare a 25% emulsifiable concentrate:
25 parts of active substance
2.5 parts of epoxidised vegetable oil
10 parts of an alkylarylsulphonate/fatty alcohol polyglycol ether mixture
5 parts of dimethyl formamide
57.5 parts of xylene.
By diluting such concentrates with water it is possible to manufacture emulsions of the desired concentration, which are especially suitable for leaf application.

The following Examples will serve to illustrate the invention in more detail, but do not restrict it to what is described therein.

EXAMPLE 1

Manufacture of N-(1'-Methylthiocarbonyl-ethyl)-N-(β-chloroethylcarbonyl)-2-methyl-6-ethylaniline of the formula

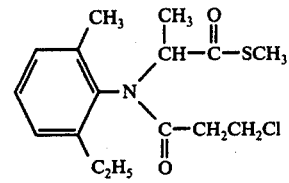

a. Preparation of the starting material: N-(1'-methylthiocarbonyl-ethyl)-2-methyl-6-ethyl-aniline A mixture of 27g of 6-ethyl-2-methylaniline, 40 g of thiomethyl 2-bromopropionate, 18.4 g of sodium bicarbonate and 100 ml of chlorobenzene was refluxed for 24 hours, cooled, diluted with 150 ml of water, and extracted with diethyl ether. The extract was dried over sodium sulphate and filtered. The ether and chloroform were evaporated and the crude product was distilled in vacuo; b.p. 170°–174° C/14 Torr.

b. With stirring, 15.2 g of 3-chloropropionic chloride in 100 ml of absolute toluene were added dropwise at room temperature to 23.7 g of the thiomethyl ester obtained in (a) in 200 ml of absolute toluene. After the weakly exothermic reaction had subsided, stirring was continued for 10 hours. The reaction mixture was subsequently refluxed for 2 hours, then cooled, washed with 10 ml of a saturated solution of sodium carbonate and twice with a small amount of water, dried over sodium sulphate and filtered. After evaporation of the toluene, the residue was crystallised by trituration with petroleum ether. After recrystallisation from petroleum ether, the compound had a melting point of 79°–81° C.

EXAMPLE 2

Manufacture of N-(1'-methylthiocarbonyl)-ethyl)-N-butyryl-2,6-dimethylaniline of the formula

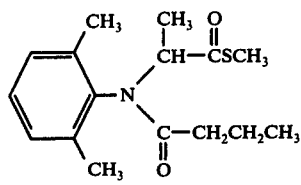

a. Preparation of the starting material: N-(1'-methyl-thiocarbonyl-ethyl)-2,6-dimethylaniline A mixture of 24.2 g of 2,6-dimethylaniline, 95.3 g of thiomethyl 2-bromopropionate and 40.2 g of sodium bicarbonate was stirred for 10 hours at 120° C, then cooled, diluted with 100 ml of water and extracted with diethyl ether. The extract was washed with a small amount of water, dried over sodium sulphate, filtered, and the ether evaporated. After excess thiomethyl 2-bromopropionate had been distilled off, the crude product was distilled in a high vacuum: b.p. 125°–127° C/0.1 Torr.

b. With stirring, 12.9 g of butyric chloride in 100 ml of absolute toluene were added dropwise in the course of 10 minutes to 22.3 g of the thiomethyl ester obtained in a) in 200 ml of absolute toluene. After the weakly exothermic reaction had subsided, stirring was continued for 10 hours at room temperature. The reaction mixture was subsequently refluxed for 2 hours, then cooled, washed with 10 ml of a saturated solution of sodium carbonate and a small amount of water, dried over sodium sulphate and filtered. After evaporation of the toluene, the residual oil was crystallised by trituration with a small amount of petroleum ether. After recrystallisation from petroleum ether, the white crystals had a melting point of 101°–102° C. The following compounds listed in Table A are manufactured in analogous manner or by one of the methods described herein:

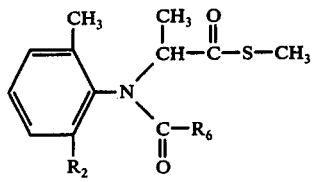

TABLE A

| | | R₂ = 6-position | |
|---|---|---|---|
| Compound | $R_2$ | $R_6$ | Physical constant (temperatures in ° C) |
| 1 | $CH_3$ | H | b.p.150–155°/0.04 Torr |
| 2 | $CH_3$ | $-CH_2CN$ | b.p.157–161°/0.08 Torr |
| 3 | $CH_3$ | $-CH_2SCN$ | b.p.165–167°/0.02 Torr |
| 4 | $CH_3$ | $-CH_2CH_3$ | b.p.145–148°/0.08 Torr |
| 5 | $CH_3$ | $-CH_2CH_2Cl$ | m.p. 84–85° |
| 6 | $CH_3$ | $-CHClCH_3$ | b.p.152–155°/0.1 Torr |
| 7 | $CH_3$ | $-CHBrCH_3$ | |
| 8 | $CH_3$ | $-CH(I)-CH_3$ | b.p.157–163°/0.1 Torr |
| 9 | $CH_3$ | $C_3H_7(n)$ | m.p. 101–102° |
| 10 | $CH_3$ | $-(CH_2)_2CH_2Cl$ | |
| 11 | $CH_3$ | $C_4H_9(t)$ | |
| 12 | $CH_3$ | $C_6H_{13}(n)$ | b.p.168–172°/0.02 Torr |
| 13 | $CH_3$ | $-CH=CH_2$ | b.p.145–148°/0.02 Torr |
| 14 | $CH_3$ | $-C=CH_2$ ⏐ Br | |
| 15 | $CH_3$ | $-CH=CH-CH_3$ | m.p. 109–113° |
| 16 | $CH_3$ | $-C\equiv C$ | m.p. 125–127° |
| 17 | $CH_3$ | ◁ | m.p. 110–111° |
| 18 | $C_2H_5$ | H | |
| 19 | $C_2H_5$ | $-CH_2CH_2Cl$ | m.p. 79–81° |
| 20 | $C_2H_5$ | $C_3H_7(n)$ | b.p.139–143°/0.3 Torr |
| 21 | $C_2H_5$ | $-(CH_2)_2CH_2Cl$ | |

TABLE A-continued

| | | R₂ = 6-position | |
|---|---|---|---|
| Compound | $R_2$ | $R_6$ | Physical constant (temperatures in ° C) |
| 22 | $C_2H_5$ | $-CHClCH(CH_3)_2$ | |
| 23 | $C_2H_5$ | $-CH=CH_2$ ⏐ Br | m.p.103–108° |
| 24 | $C_2H_5$ | $-CH=CH-CH_3$ | b.p.155–6°/0.02 Torr |
| 25 | $C_2H_5$ | ◁ | |
| 26 | $CH_3O$ | $-CH_2SCN$ | b.p.164–170°/0.02 Torr. |
| 27 | $CH_3O$ | $-CH_2CH_3$ | |
| 28 | $CH_3O$ | $-CH_2CH_2Cl$ | b.p.154–157°/0.04 Torr. |
| 29 | $CH_3O$ | $C_3H_7(n)$ | |
| 30 | $CH_3O$ | $-CH=CH_2$ | |
| 31 | $CH_3O$ | $-CH=CH-CH_3$ | b.p.171–173°/0.08 Torr. |
| 32 | $CH_3O$ | ◁ | |
| 33 | Cl | $-CH_2SCN$ | |
| 34 | Cl | $-CH_2CH_2Cl$ | b.p.170–172°/0.1 Torr. |
| 35 | Cl | $C_3H_7(n)$ | |
| 36 | Cl | $-CH=CH-CH_3$ | |
| 37 | Cl | ◁ | b.p.168–171°/0.08 Torr. |

The compounds listed in Table B are also manufactured in analogous manner or by one of the methods described herein:

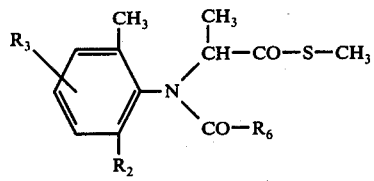

TABLE B

| | | R₂ = 6-position | | |
|---|---|---|---|---|
| Compound | $R_2$ | $R_3$ | $R_6$ | Physical constant (temperatures in ° C) |
| 38 | $CH_3$ | 3-$CH_3$ | $-CH_2CH_2Cl$ | m.p. 68–70° |
| 39 | $CH_3$ | 3-$CH_3$ | $C_3H_7(n)$ | |
| 40 | $CH_3$ | 3-$CH_3$ | $-CH=CH-CH_3$ | b.p.167–169°/0.07 Torr. |
| 41 | $CH_3$ | 3-$CH_3$ | ◁ | |
| 42 | $CH_3$ | 4-$CH_3$ | $-CH_2CH_2Cl$ | m.p. 102–103° |
| 43 | $CH_3$ | 4-$CH_3$ | $C_3H_7(n)$ | m.p. 78° |
| 44 | $CH_3$ | 4-$CH_3$ | $-CH=CH-CH_3$ | |
| 45 | $CH_3$ | 4-$CH_3$ | ◁ | m.p. 109–110° |
| 46 | $CH_3$ | 4-$C_3H_{7(i)}$ | $-CH_2CH_2Cl$ | |
| 47 | $CH_3$ | 3-Br | $-CH_2CH_2Cl$ | b.p.176–178°/0.05Torr. |
| 48 | $CH_3$ | 3-Br | $C_3H_7(n)$ | |
| 49 | $CH_3$ | 3-Br | $-CH=CHCH_3$ | b.p.170–175°/0.08Torr. |
| 50 | $CH_3$ | 3-Br | ◁ | |
| 51 | $CH_3$ | 4-Cl | $CH_2CH_2Cl$ | b.p.165–168°/0.04Torr. |
| 52 | $CH_3$ | 4-Cl | $CHClCH_3$ | |
| 53 | $CH_3$ | 4-Cl | $C_3H_7(n)$ | |
| 54 | $CH_3$ | 4-Br | $CH_2CH_2Cl$ | b.p.182–184°/0.02Torr. |
| 55 | $CH_3$ | 4-Br | $-CH=CH-CH_3$ | |
| 56 | $C_2H_5$ | 3-$CH_3$ | $CH_2CH_2Cl$ | b.p.171–174°/0.08Torr. |

The following compounds listed in Table C are also manufactured in analogous manner or by one of the methods described herein:

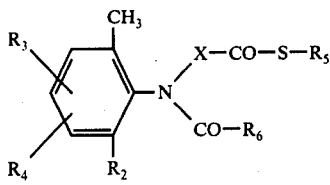

TABLE C

| | | | | $R_2$ = 6-position | | |
|---|---|---|---|---|---|---|
| Compound | $R_2$ | $R_3$ | $R_4$ | X | $R_5$ | $R_6$ | Physical constant (temperatures in °C) |
| 57 | $CH_3$ | 3-$CH_3$ | 5-$CH_3$ | —CH($CH_3$)— | $CH_3$ | —$CH_2CH_2Cl$ | m.p.132–133° |
| 58 | $CH_3$ | 3-$CH_3$ | 5-$CH_3$ | —CH($CH_3$)— | $CH_3$ | —CHCl—$CH_3$ | |
| 59 | $CH_3$ | 3-$CH_3$ | 5-$C_3$ | —CH($CH_3$)— | $CH_3$ | —$C_3H_7$(n) | b.p.185°/0.02Torr. |
| 60 | $CH_3$ | H | H | —CH($CH_3$)— | $C_2H_5$ | —$CH_2CH_2Cl$ | b.p.170°/0.02Torr. |
| 61 | $CH_3$ | H | H | —CH($CH_3$)— | $C_2H_5$ | —$C_3H_7$(n) | |
| 62 | $CH_3$ | H | H | —CH($CH_3$)— | $C_2H_5$ | —CH=CH—$CH_3$ | b.p.188°/0.04Torr. |
| 63 | $CH_3$ | H | H | —CH($CH_3$)— | $C_2H_5$ | ◁ | |
| 64 | $C_2H_5$ | H | H | —CH($CH_3$)— | $C_2H_5$ | —$CH_2CH_2Cl$ | |
| 65 | $CH_3$ | H | H | —$CH_2$— | $CH_3$ | —$CH_2CH_2Cl$ | b.p.164°/0.08Torr. |
| 66 | $CH_3$ | H | H | —$CH_2$— | $CH_3$ | —CHCl—$CH_3$ | |
| 67 | $CH_3$ | H | H | —$CH_2$— | $CH_3$ | —$C_4H_9$ (tert.) | |
| 68 | $C_2H_5$ | H | H | —$CH_2$— | $CH_3$ | —$CH_2CH_2Cl$ | |
| 69 | $CH_3$ | H | H | —$CH_2$— | $C_2H_5$ | —$CH_2CH_2Cl$ | b.p.176°/0.1 Torr. |
| 70 | Cl | H | H | —$CH_2$— | $C_2H_5$ | —$CH_2CH_2Cl$ | b.p.184°/0.08Torr. |
| 71 | $CH_3$ | 3-$CH_3$ | H | —$CH_2$— | $C_2H_5$ | —$CH_2CH_2Cl$ | |
| 72 | $CH_3$ | 3-$CH_3$ | 5-$CH_3$ | —$CH_2$— | $C_2H_5$ | —$CH_2CH_2Cl$ | |
| 73 | $CH_3$ | H | H | —CH($CH_3$)— | $CH_3$ | —$CH_2$—$CH_2$—CN | m.p. 85–88° |
| 74 | $CH_3$ | H | H | —CH($CH_3$)— | $CH_3$ | —$CH_2$—CH—SCN | m.p. 104° |
| 75 | Cl | H | H | —CH($CH_3$)— | $CH_3$ | —$CH_2$—$CH_2$—CN | m.p. 108–111° |

Derivatives of N-carboxymethyl-2,4,6-triido-acetanilide are described as roentgenographic contrast agents in U.S. Pat. No. 3,048,626 and in U.S. Pat. No. 3,413,340.

N-Acetyl-N-phenyl-glycinamides are disclosed as antipyretics and analgesics in British Pat. No. 895,693.

N-(3-chloro-4-methacryloylphenyl)-N-acetyl-glycine is disclosed in Netherlands published patent specification 65/002,404 as belonging to a group of N-methacryloylphenyl-glycines to which a diuretic action is ascribed.

The commercially available selective herbicide N-benzoyl-N(3,4-dichlorophenyl-)aniline-ethyl ester is known from U.S. patent 3,712,805 from a group of herbicidally active N-phenyl-glycine esters.

To none of these different compound structures has a fungicidal property been ascribed. The closest comparable compounds disclosed in U.S. Pat. No. 3,712,805 without exception possess no fungicidal action.

It is therefore very surprising that the special class of compounds of the formula I of the present invention, as the following tests show, have a pronounced fungicidal action on plants but do not possess any herbicidal properties. This feature makes the compounds of the present invention particularly suitable for plant protection.

EXAMPLE 3

Action on Phytophthora infestans on tomato plants

Ia. Residual preventive action

Solanum lycopersicum plants of the "Roter Gnom" variety are infected when 3 weeks old with a zoospore suspension of Phytophthora infestans after they have been sprayed with a broth (prepared from the active substance formulated as a wettable powder) and containing 0.05% of active substance, and dried. They are then kept for 6 days in a climatic chamber at 18° to 20° C and high humidity, which is produced with an artificial wet fog. After this time typical leaf specks appear. The effectiveness of the tested substance is assessed by determining in the number and size of these specks.

Ib. Curative action

"Roter Gnom" tomato plants are sprayed when 3 weeks old with a zoospore suspension of the fungus and incubated in a climatic chamber at 18° to 20° C and saturated humidity. The humidifying is interrupted after 24 hours. After the plants have been dried, they are sprayed with a broth which contains the active substance formulated as a wettable powder in a concentration of 0.05%. After the spray coating has dried, the plants are again kept in the humid chamber for 4 days. The effectiveness of the tested substances is assessed by determining the size and number of the typical leaf specks which have occurred during this time.

II. Preventive-systemic action

The active substance is applied as a wettable powder in a concentration of 0.05% (referred to the volume of the soil) to the surface of the soil of 3 week old "Roter Gnom" tomatoes in pots. Three days later the underside of the leaves of the plants are sprayed with a zoospore suspension of Phytophthora infestans. The plants are then kept in a spray chamber at 18° to 20° C and saturated humidity for 5 days, after which time typical leaf specks form. The effectiveness of the tested substances is assessed by determining the size and number of these specks. Compared with untreated, infected control plants (=100% fungus attack), the plants treated with the active substances of the formula I were attacked by fungus to only an insignificant extent. Application of compounds 5, 9, 15, 20, 28, 29, 31, 32, 34, 35, 36, 37, 38, 39, 40, 41, 47, 57, 60, 73 and 75 reduced the attack to below 20%.

EXAMPLE 4

Action on Plasmopara viticola (Bert. et Curt.) (Berl. et de Toni) on vines a. Residual preventive action Vine cuttings of the variety "Chasselas" were reared in a greenhouse. Three plants in the 10 leaf stage were sprayed with a broth (0.05% of active substance) prepared from the active substance and formulated as a wettable powder. After the coating layer had dried, the plants were infected on the underside of the leaves with the spore suspension of the fungus. The plants were subsequently kept in a humid chamber for 8 days, after which time symptoms of the disease were visible on the control plants. The effectiveness of the tested substances was assessed by determining the number and size of the infected areas on the treated plants.

b. Curative action

Vine cuttings of the variety "Chasselas" were reared in a greenhouse and infected in the 10 leaf stage with a spore suspension of Plasmopara viticola on the underside of the leaves. After they had been kept for 24 hours in a humid chamber, the plants were sprayed with a 0.05% active substance broth prepared from a wettable powder of the active substance.

The plants were then kept in a humid chamber for a further 7 days, after which time the symptoms of the disease were visible on the control plants. The effectiveness of the tested substances was assessed by determining the number and size of the infected areas on the treated plants.

Compared with untreated, infected control plants, (=100% fungus attack), the compounds of the formula Ia exhibited good leaf fungicidal action in these two tests. The fungus attack was controlled completely or almost completely (0–5%) with the compounds of groups Ib and Ic. Even when used in an active substance concentration of only 0.02%, compounds 5, 9, 15, 17, 20, 24, 38, 42, 43, 57, 73 and 75 inhibited the attack to 0–5%.

In the control of downy mildew, those compounds of group Ib are preferred in which $R_3$ represents hydrogen, methyl, fluorine, chlorine or bromine, $R_5$ represents methyl and $R_6$ represents n-propyl, β-chloroethyl or β-cyanoethyl whilst $R_1$, $R_2$, $R_4$ and X are as defined previously herein.

EXAMPLE 5

Action against Pythium debaryanum on Beta vulgaris (sugarbeet)

a. Action after soil application

The fungus is cultivated on sterile oat kernels and added to a mixture of earth and sand. Flower pots are filled with the infected soil in which sugar beet seeds are then sown. Immediately after sowing, the test preparations formulated as wettable powders are poured in the form of aqueous suspensions over the soil (20 ppm of active substance referred to the volume of the soil). The pots are then stood for 2–3 weeks in a greenhouse at 20°–24° C. The soil is kept uniformly moist by gently spraying it with water. The emergence of the sugar beet plants as well as the number of healthy and sick plants are ascertained in evaluating the tests.

b. Action after seed dressing

The fungus is cultivated on sterile oat kernels and added to a mixture of earth and sand. Flower pots are filled with the infected soil and sugar beet seeds which have been treated with the test preparations formulated as seed dressing powders are sown therein (1000 ppm of active substance, referred to the weight of the seeds). The pots are then stood in a greenhouse for 2–3 weeks at 20°–24° C. The soil is kept uniformly moist by gently spraying it with water. The emergence of the sugar beet plants as well as the number of healthy and sick plants are ascertained.

Under the conditions of both test (a) and test (b), more than 80% of the sugar beet plants emerged after treatment with the active substances of the formula I and had a healthy appearance.

We claim:

1. A compound of the formula

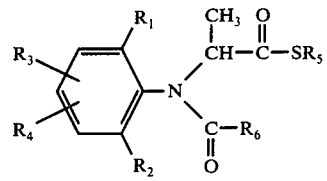

wherein
$R_1$ represents methyl or methoxy,
$R_2$ represents methyl, ethyl, chlorine or bromine,
$R_3$ represents hydrogen, methyl or halogen,
$R_4$ represents hydrogen or methyl,
$R_5$ represents methyl or ethyl, and
$R_6$ represents hydrogen, $C_2$ or $C_3$ alkyl, $C_1$–$C_3$ alkyl substituted by cyano or thiocyano, $C_2$ or $C_3$ alkyl substituted by halogen, $C_2$–$C_4$ alkenyl, $C_2$–$C_4$ alkenyl substituted by halogen, $C_2$–$C_4$ alkynyl or $C_3$–$C_7$ cycloalkyl.

2. A compound according to claim 1, wherein
$R_3$ represents hydrogen, methyl, fluorine, chlorine or bromine,
$R_5$ represents methyl, and
$R_6$ represents n-propyl, β-chloroethyl or β-cyanoethyl.

3. N-(1'-Methylthiocarbonyl-ethyl)-N-β-chloropropionyl-2,6-dimethylaniline according to claim 2.

4. N-(1'-Methylthiocarbonyl-ethyl)-N-β-chloropropionyl-2,3,6-trimethylaniline according to claim 2.

5. A compound of the formula

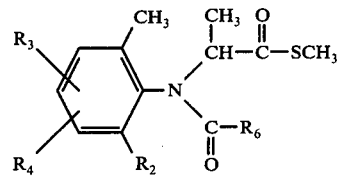

wherein
$R_2$ represents methyl, ethyl or chlorine,
$R_3$ represents hydrogen, $C_1$–$C_3$ alkyl or halogen,
$R_4$ represents hydrogen or methyl, and
$R_6$ represents $C_2$–$C_4$ alkyl, $C_2$–$C_4$ alkenyl or cyclopropyl, with the proviso that the total number of carbon atoms in $R_2$, $R_3$ and $R_4$ does not exceed 3.

6. A composition for controlling phytopathogenic fungi which comprises (1) as active ingredient, a compound according to claim 1 and (2) a carrier.

7. A composition for controlling phytopathogenic fungi which comprises (1) as active ingredient, a compound according to claim 2 and (2) a carrier.

8. A composition for controlling phytopathogenic fungi which comprises (1) as active ingredient, the compound according to claim 3 and (2) a carrier.

9. A composition for controlling phytopathogenic fungi which comprises (1) as active ingredient, the compound according to claim 4 and (2) a carrier.

10. A composition for controlling phytopathogenic fungi which comprises (1) as active ingredient, a compound according to claim 5 and (2) a carrier.

11. A method for protecting plants from phytopathogenic fungi which comprises applying to growing plants, to soil in which plants are to be grown or to seeds of the plants, in an amount sufficient to protect the plants from fungi, a compound of the formula

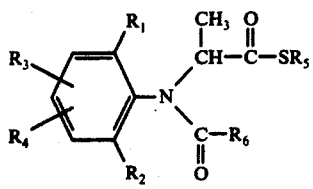

wherein
$R_1$ represents methyl or methoxy,
$R_2$ represents methyl, ethyl, chlorine or bromine,
$R_3$ represents hydrogen, methyl or halogen,
$R_4$ represents hydrogen or methyl,
$R_5$ represents methyl or ethyl, and
$R_6$ represents hydrogen, $C_2$ or $C_3$ alkyl, $C_1$-$C_3$ alkyl substituted by cyano or thiocyano, $C_2$ or $C_3$ alkyl substituted by halogen, $C_2$-$C_4$ alkenyl, $C_2$-$C_4$ alkenyl substituted by halogen, $C_2$-$C_4$ alkynyl or $C_3$-$C_7$ cycloalkyl.

12. A method according to claim 11 in which
$R_3$ represents hydrogen, methyl, fluorine, chlorine or bromine,
$R_5$ represents methyl, and
$R_6$ represents n-propyl, $\beta$-chloroethyl or $\beta$-cyanoethyl.

13. The method according to claim 12 in which the compound is N-(1'-methylthiocarbonyl-ethyl)-N-$\beta$-chloropropionyl-2,6-dimethylaniline.

14. The method according to claim 12 in which the compound is N-(1'-methylthiocarbonyl-ethyl)-N-$\beta$-chloropropionyl-2,3,6-trimethylaniline.

15. A method for protecting plants from phytopathogenic fungi which comprises applying to growing plants, to soil in which plants are to be grown, or to seeds of the plants, in an amount sufficient to protect the plants from fungi, a compound of the formula

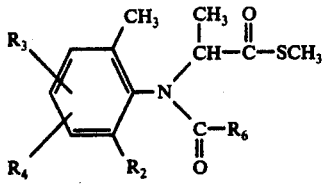

wherein
$R_2$ represents methyl, ethyl or chlorine,
$R_3$ represents hydrogen, $C_1$-$C_3$ alkyl or halogen,
$R_4$ represents hydrogen or methyl,
$R_6$ represents $C_2$-$C_4$ alkyl, $C_2$-$C_4$ alkenyl or cyclopropyl, with the proviso that the total number of carbon atoms in $R_2$, $R_3$ and $R_4$ does not exceed 3.

16. A method for combatting phytopathogenic fungi which comprises applying to growing plants a fungicidally effective amount of a compound of the formula

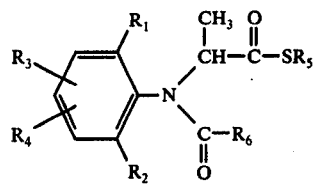

wherein
$R_1$ represents methyl or methoxy,
$R_2$ represents methyl, ethyl, chlorine or bromine,
$R_3$ represents hydrogen, methyl or halogen,
$R_4$ represents hydrogen or methyl,
$R_5$ represents methyl or ethyl, and
$R_6$ represents hydrogen, $C_2$ or $C_3$ alkyl, $C_1$-$C_3$ alkyl substituted by cyano or thiocyano, $C_2$ or $C_3$ alkyl substituted by halogen, $C_2$-$C_4$ alkenyl, $C_2$-$C_4$ alkenyl substituted by halogen, $C_2$-$C_4$ alkynyl or $C_3$-$C_7$ cycloalkyl.

17. A method according to claim 16 in which
$R_3$ represents hydrogen, methyl, fluorine, chlorine or bromine,
$R_5$ represents methyl, ethyl and
$R_6$ represents n-propyl $\beta$-chloroethyl or $\beta$-cyanoethyl.

18. The method according to claim 17 in which the compound is N-(1'-methylthiocarbonyl-ethyl)-N-$\beta$-chloropropionyl-2,6-dimethylaniline.

19. The method according to claim 17 in which the compound is N-(1'-methylthiocarbonyl-ethyl)-N-$\beta$-chloropropionyl-2,3,6-trimethylaniline.

20. A method for combatting phytopathogenic fungi which comprises applying to growing plants a fungicidally effective amount of a compound of the formula

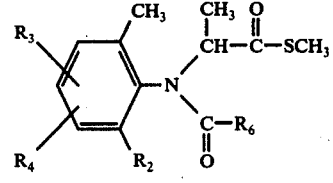

wherein
$R_2$ represents methyl, ethyl or chlorine,
$R_3$ represents hydrogen, $C_1$-$C_3$ alkyl or halogen,
$R_4$ represents hydrogen or methyl, and
$R_6$ represents $C_2$-$C_4$ alkyl, $C_2$-$C_4$ alkenyl or cyclopropyl,
with the proviso that the total number of carbon atoms in $R_2$, $R_3$ and $R_4$ does not exceed 3.

* * * * *